(12) United States Patent
Silverman et al.

(10) Patent No.: US 8,329,007 B2
(45) Date of Patent: Dec. 11, 2012

(54) HEARING AID DEHUMIDIFIER AND DISINFECTANT CHAMBER

(75) Inventors: Martin S. Silverman, Camarillo, CA (US); Lance Pritikin, Camarillo, CA (US)

(73) Assignee: MB Research & Development, LLC, Temecula, CA (US)

( * ) Notice: Subject to any disclaimer, the term of this patent is extended or adjusted under 35 U.S.C. 154(b) by 1770 days.

(21) Appl. No.: 11/470,608

(22) Filed: Sep. 6, 2006

(65) Prior Publication Data

US 2007/0207071 A1    Sep. 6, 2007

Related U.S. Application Data

(60) Provisional application No. 60/714,570, filed on Sep. 7, 2005.

(51) Int. Cl.
*C25B 9/00* (2006.01)
(52) U.S. Cl. ............... 204/275.1; 204/242; 204/252; 204/263; 205/628
(58) Field of Classification Search .............. 205/626; 204/242, 252, 263, 275.1
See application file for complete search history.

(56) References Cited

U.S. PATENT DOCUMENTS

| | | | |
|---|---|---|---|
| 4,541,989 A * | 9/1985 | Foller | 422/186.07 |
| 2003/0080467 A1 * | 5/2003 | Andrews et al. | 264/275 |
| 2003/0196687 A1 * | 10/2003 | Campbell et al. | 134/35 |
| 2005/0095498 A1 * | 5/2005 | Silverman | 429/61 |

FOREIGN PATENT DOCUMENTS
JP    11180702 A  *  7/1999

\* cited by examiner

*Primary Examiner* — Nicholas A. Smith
(74) *Attorney, Agent, or Firm* — Fulwider Patton LLP (57) ABSTRACT

A hearing aid dehumidifier and disinfectant chamber. The chamber comprises an enclosure, including a vapor permeable wall, adapted to removably enclose a hearing aid. In vapor transmitting relationship with the vapor permeable wall is an electrochemical ozone generator, which is designed to draw water vapor from inside the enclosure and electrolyze it into at least ozone, which is discharged into the enclosure. Drawing the water vapor from the enclosure dries the hearing aid. The electrochemical action ceases when all water vapor is removed. Bathing the hearing aid in ozone for at least until the ozone decomposes, sterilizes the hearing aid, inside and out.

18 Claims, 8 Drawing Sheets

HEARING AID DEHUMIDIFIER AND DISINFECTANT CHAMBER

CROSS REFERENCE TO RELATED APPLICATIONS

This application claims the benefit of U.S. Provisional Application No. 60/714,570, filed Sep. 7, 2005. The disclosures of U.S. patent application Ser. No. 10/976,490, now U.S. Pat. No. 7,705,558, filed Oct. 29, 2004, and 60/516,205, filed Oct. 31, 2003, and 60/714,570 are hereby incorporated by reference as though fully set forth herein. U.S. patent application Ser. No. 10/976,490, now U.S. Pat. No. 7,705,558, and 60/516,205 concern recharging of hearing aid batteries by electromagnetic energy.

BACKGROUND OF THE INVENTION

1. Field of the Invention

The invention relates in general to methods and devices for disinfecting and dehumidifying hearing aids, and, more particularly, embodiments of the present invention relate to electrolytic drying and ozone generating methods and devices for sterilizing and dehumidifying hearing aids.

2. Description of the Prior Art

It is well known that hearing aids accumulate water and become biologically contaminated with use. The water is detrimental to the electronic components of the hearing aid. The biological contamination is detrimental to the wearer of the hearing aid. Audio quality is seriously impaired if a hearing aid is humid and contaminated. Previous proposals for dealing with these problems include Schumaier U.S. Pat. No. 5,852,879. Schumaier proposes to dry hearing aids by placing them in a sealed chamber together with a regeneratable desiccant such as silica gel. He further proposes to sterilize the hearing aids with a germicidal lamp that emits radiation in the UV region. Schumaier states that when a UV lamp is used ozone is produced. This ozone is said to act as a deodorizer while the direct radiation kills the bacteria. The need to frequently regenerate or replace the desiccant limits the utility of this proposed system. Treatment with UV radiation is a line of sight process. Areas that are shaded from direct exposure to the UV radiation do not receive treatment. Reliance on UV radiation for germicidal treatment requires physically turning the hearing aid so as to expose all of its surfaces to direct UV radiation. In addition, spaces within the hearing aid are not accessed by the UV radiation and thus are not sterilized. Further, the teaching that a germicidal UV lamp will generate ozone is not clear. Germicidal lamps typically produce ultraviolet light in a narrow spectral band centered at 254 nanometers. It is known that ozone is not generated at this frequency. In fact, Ozone is actually destroyed by ultraviolet light at 254 nanometers. Ozone is generated at an ultraviolet frequency of from about 100 to 200 nanometers, and particularly, 185 nanometers. Ultraviolet at 185 nanometers is not produced by germicidal UV lamps. See Sauska et al., U.S. Pat. No. 6,824,693, and Barnes, U.S. Pat. No. 6,893,610. See also Ted Rich; "A Basic Comparison of Ozone Technologies", Water Technology Magazine, October 1994. As germicidal UV lamps do not generate ozone, Schumaier's invention, by definition, is not capable of sterilizing a hearing aid by generation of and exposure to ozone.

These and other limitations seriously impair the utility of the previously proposed expedients.

U.S. Pat. No. 5,640,783, also to Schumaier, discloses a dryer appliance for demoisturizing a moisture sensitive item such as an electronic hearing aid or the like, having a housing with a removable cap for providing a substantially sealed chamber and access thereto, a desiccant component mounted in the housing and substantially dividing the chamber into first and second regions, a support in the chamber for supporting at least one item within the first region, one or more passages interconnecting the first and second regions for providing a gas flow circulation path therethrough, the circulation path being (a) gas flow into contact with and through the desiccant component, (b) then into and thru the first region for contact with the item, (c) then thru the passage into the second region, and (d) then again into contact with the desiccant component to continue the circulation, and a gas moving mechanism in the chamber for forcing and maintaining the gas flow circulation path.

The Schumaier invention is sold commercially under the name Dry and Store® and is available from Dry & Store, P.O. Box 1017, Johnson City, Tenn. 37605.

The electrochemical generation of ozone by the electrolysis of water is well known. See, for example, Murphy, U.S. Pat. No. 5,460,705, and Foller et al., U.S. Pat. No. 4,316,782. The efficiency of ozone generation may be increased by the proper selection of electrode material and electrolyte.

U.S. Pat. No. 4,316,782 (Foller) teaches that ozone yields as high as 52% could be obtained where the electrolyte is water and either the acid or salt form of highly electronegative anions, such as hexafluouro-anions are used. Here, the term "fluoro-anions" is used to describe that family of anionic (negatively charged) species in which multiple fluorine ligands complex a central atom. Electrolysis was carried out in a range between room temperature and the freezing point of water. The preferred anode materials for use in the electrolytic cells are either platinum or lead dioxide, especially lead dioxide in the beta crystalline form. Platinum, carbon, or nickel and its alloys may be used as hydrogen-evolving cathodes. Alternatively, an air or oxygen depolarized cathode may be employed which would greatly reduce the cell voltage and enhance the overall energy efficiency of the process.

Such electrolytic solutions can be highly corrosive to the cell materials if they are not selected properly, and especially hard on the electrodes where electrochemical discharge takes place. In addition, the liberated $O_3$, being a powerful oxidizing agent, also strongly acts upon electrode materials which are susceptible to oxidizing action. The electrical properties of the electrode material are also important to the successful and effective operation of the ozone generating electrolytic cell. The electrodes must exhibit sufficient electrical conductivity to enable the utilization of current densities required by the ozone generating process without an unacceptable anode potential and must also be adaptable to whatever cooling procedures are required to maintain cell temperatures during operation.

Foller also disclosed that using an air or oxygen depolarized cathode provided several advantages. (1) The cell voltage would be substantially reduced since replacing hydrogen evolution with the reduction of oxygen theoretically saves 1.23 volts. (In actual practice, a 0.8 volt swing is likely to be achieved.) (2) A separator between anode and cathode is no longer required, as no hydrogen is evolved to depolarize the anode. Further, savings in cell voltage are obtained by reducing IR losses. (3) The overall cell process becomes oxygen in and ozone out and the need for periodic additions of water is reduced. (4) The same air or oxygen fed to the air cathode could also serve to dilute and carry off the ozone that is anodically evolved by flowing through the cathode.

Air cathode technology has found recent favor in its application to fuel cells, metal-air batteries, and the chlor-alkali industry. The electrodes are generally composed of Teflon-bonded carbon containing small amounts of catalytic materials.

U.S. Pat. No. 4,375,395 (Foller) teaches that anodes made of glassy carbon are suitable for use in the preparation of ozone in an electrolytic cell utilizing an aqueous solution of the highly electronegative, fluoro-anions.

U.S. Pat. No. 4,541,989 (Foller) teaches that a liquid electrolyte containing acids of fluoro-anions, such as $HBF_4$ and $HPF_6$, used in combination with a cool electrolyte solution can increase the efficiency and the ozone to oxygen yield. However, the use of a liquid electrolyte causes some problems. First, the electrodes in such electrolytic cell must be separated by a given distance to provide definition. This translates into power loss in the production of heat. Secondly, the presence of liquid electrolytes requires a sophisticated system of seals to prevent leaking of the electrolyte.

U.S. Pat. No. 4,836,929 (Laumnn et al.) teaches the use of a solid electrolyte such as that made by duPont and sold under the brand "NAFION". This solid electrolyte was placed between a lead dioxide anode and a platinum black cathode. The current efficiency was increased by oxygenating a water stream fed to the anode and the cathode. In this manner, oxygen could be reduced to water at room temperature releasing an increased yield of ozone.

In his paper entitled "Synthesis of Hydrogen Peroxide in a Proton Exchange Membrane Electrochemical Reactor" (April 1993), Fenton disclosed that paired synthesis of ozone ($O_3$) and hydrogen peroxide ($H_2O_2$) could be carried out in the same reactor. The electrochemical reactor used a membrane and electrode assembly (M&E) comprised of a "NAFION" 117 membrane between the platinum black/polytetrafluoroethylene (PTFE) anode and graphite/PTFE cathode. This M&E assembly was sandwiched between a carbon fiber paper (Toray Industries) on the cathode side and a platinum mesh (52 mesh, Fisher Scientific) on the anode side, which were used as current collectors. This arrangement was alleged to produce some hydrogen peroxide.

Increasing the percentage of PTFE in the electrode increases the hydrophobicity of the electrode assembly and thus allows more of the gaseous reactant to reach the electrode surface by repelling the products formed. The graphite M&E with 20% PTFE produced slightly higher hydrogen peroxide than a similar M&E with 10% PTFE. This could be due to the mass transport limitation of oxygen to the membrane and electrode assembly within the less hydrophobic 10% M&E. It is preferred that the PEM reactor operate at potentials greater than 3.0 volts where the anodic evolution of ozone is favored.

Membranes containing perfluorinated sulphonic acids are typically prepared before use in an electrochemical cell by first soaking the membrane in hot water for about 30 minutes and then soaking it in 10% HCl to ensure that the entire membrane is in the H.sup.+ form. The membrane has to be kept moist at all times as it acts as a conductor only when it is wet. It is preferred that the proton exchange membrane be pretreated with an aqueous solution of sulphuric acid followed by rinsing the proton exchange membrane with pure water, rinsing the proton exchange membrane with an aqueous solution of hydrogen peroxide, and rinsing the proton exchange membrane with a final rinse of pure water. The final rinse should be made at a temperature between 50° C. and 150° C. and under pressure.

In their paper entitled "Paired Synthesis of Ozone and Hydrogen Peroxide in an Electrochemical Reactor," Pallav Tatapudi and James Fenton explain that the benefits of paired synthesis in electrolyte free water include: (1) lower energy consumption costs, as two oxidizing agents can be obtained for the price of one; (2) the elimination of the need for transportation and storage of oxidants by generating them electrochemically within water on demand at an amount proportional to the waste concentration; and (3) higher aqueous phase ozone concentrations.

U.S. Pat. No. 4,416,747 (Menth et al.) discloses an individual electrolysis cell bounded by bipolar plates and having a solid electrolyte made of perfluorinated sulphonic acids ("NAFION" by duPont) with a surface coating centrally located between current-collectors and adjoining open metallic structures. A plurality of individual cells may be integrated together between end plates so that the cells are electrically connected in series, hydrodynamically connected in parallel, and combined to form a block.

The current collectors disclosed in Menth may be close-meshed expanded metal covered by an open structure having a low resistance to the flow of a liquid in the direction parallel to the planar structure. The current collectors are preferably made from titanium. The ends of the cell are formed, in each case, by a bipolar plate, which alternately acts as a cathode and as an anode. The bipolar plate is preferably made from stainless (Cr/Ni) steel. The space or chamber between the bipolar plates and the solid electrolyte is completely filled with water in which air or oxygen is suspended and/or dissolved.

The Menth assembly of the electrolysis cells basically corresponds to the filter-press type, with the liquid passing parallel to the principal planes of the cells instead of perpendicularly. The individual cells are held together between two end plates having electrical terminals, thereon.

The method and apparatus disclosed in Menth, however, can support only limited current density associated with reduction-oxidation, since oxygen has only limited solubility in water. Further, since the cathode chamber is filled with liquid water, the cathode electrode structure will become flooded with water. Higher current densities are desirable to cause an increase in the ozone production efficiency.

U.S. Pat. No. 4,836,949 (Laumann et al.) teaches a process for breaking down organic substances and/or microbes in pretreated feed water for high-purity recirculation systems using ozone which is generated in the anode chamber of an electrochemical cell and treated with ultraviolet rays and/or with hydrogen generated in the cathode chamber of the same cell or supplied from outside.

In light of the foregoing discussion, there exists a need for an economical method of producing ozone, which will minimize voltage allowed for higher current density and produce a high concentration of ozone.

The use of ozone in medical sterilization equipment in relatively high concentrations and/or high humidity environments is known. See, for example, Nagashima, U.S. Pat. No. 5,141,722, Faddis et al., U.S. Pat. No. 5,344,622, and Karlson, U.S. Pat. No. 5,868,999. These proposed systems are not suitable for home use because of the safety hazards they pose in the hands of inexperienced or inattentive operators.

The electrolytic drying of small enclosed volumes of air is known. See, for example, Hirschfield, U.S. Pat. No. 4,528,078, Suzuki et al., U.S. Pat. No. 6,547,953, Yamauchi et al., U.S. Pat. No. 5,059,291, and Bredeweg, U.S. Pat. No. 4,050,995. In such systems, generally the water vapor in the enclosure is disassociated by electrolysis into hydrogen and oxygen, but not ozone. Such systems had been proposed for use, for example, in magnetic disk drives, cameras, and electronic instrument packages.

There are numerous deficiencies with the prior art, particularly the Dry & Store®. Use of desiccant for dehumidification is inefficient. This is because the desiccant becomes wetter over time, whether it is used for dehumidification of a hearing aid or not. The desiccant is bulky and must be periodically replaced. Near the end of its dehumidification life it will not dehumidify the hearing aid to the same level of dryness.

As pointed out above, UV irradiation only works line of sight. Sterilization only occurs on surfaces that are directly irradiated by the UV light. All other areas (e.g., the underside, the sound tube, and internal components and compartments of the hearing aid) are not sterilized, but in effect are breading grounds for bacteria, molds, parasites and viruses. Further, partial or incomplete sterilization with time facilitates the evolution of highly resistant and virulent strains of such microorganisms. Moreover, as UV irradiation is a known mutagen, the use of UV irradiation increases mutagenesis within the microorganism residents of the hearing aid, which in turn increases the probability that new and more virulent stains of these microorganisms will develop on, and within the hearing aid.

It is well known that certain strains of bacteria and molds will attack and compromise various components contained within an electrical device and circuit. These components include insulation on wires, and PCB traces, PCB substrates, transducer membranes and cones, semiconductor surfaces such as those used in potentiometers (used for volume control in a variety of hearing aids), metallic contacts and fixtures, plastic components, etc. Thus the incomplete sterilization provided by the present art is non optimal and can in fact exacerbate the attack and subsequent failure of the internal components of the hearing aid.

Moreover, UV irradiation degrades the plastic body of the hearing aid and also any illuminated structural and functional components.

Finally, in the prior art sterilization and dehumidification are attempted by two separate and distinct systems requiring heaters, fans, regulators, sensors, baffles, and other intricate bulky structural components that require servicing and frequent replacement. Heating also compromises the efficiency of the desiccant, as higher temperatures will drive water out of the desiccant as well as the object to be dehumidified or desiccated. The desiccant might be regenerated by heating, but the water must have some way to escape for this to be useful. Further, such heating has deleterious effects on the hearing aid, and the zinc air battery contained within: it is well known that heat decreases the life of most batteries, including the zinc air type.

These and other difficulties of the prior art have been overcome according to the present invention.

BRIEF SUMMARY OF THE INVENTION

The present invention has been developed in response to the current state of the art, and in particular, in response to these and other problems and needs that have not been fully or completely solved by currently available expedients for drying and disinfecting hearing aids. Thus, it is an overall object of the present invention to effectively resolve at least the problems and shortcomings of the prior art identified above. The hearing aid dehumidifier and disinfectant chamber of this invention comprises an enclosure, which includes a vapor permeable wall. The enclosure is adapted to removably enclose a hearing aid. Adjacent and in vapor transmitting relationship with the vapor permeable wall is an electrochemical ozone generator. The electrochemical ozone generator is adapted to draw water vapor from inside the enclosure and electrolyze it into at least ozone, which is discharged into the enclosure. The essential reaction that takes place at the anode is as follows:

$$OH^- \rightarrow H^+ + O^{-2} \rightarrow O_2 + O_3 + H^+$$

The essential reaction that takes place at the cathode is $$H^+ \rightarrow H_2$$

Thus the overall reaction in the generator is $$(2x+3y)H_2O \rightarrow (2x+3y)H_2 + xO_2 + yO_3$$

The generator design and construction is such that at least 0.01 percent of the total evolved oxygen (x+y) is in the form of ozone.

The electrochemical ozone generator preferably comprises: a wire mesh anode, a wire mesh cathode, an absorbent, electrically non-conductive, and chemically inert separator, interposed between them and a hygroscopic electrolyte adsorbed onto said separator. The separator may or may not be hydrophilic. The wire mesh is inert to the electrical and chemical environment of the electrochemical ozone generator. Preferably the wire is nichrome, nichrome plated with platinum, stainless steel or stainless steel onto which lead dioxide is impressed. Preferably the electrolyte is potassium hydroxide. Optionally the electrolyte also contains a non-hygroscopic electrolyte possessing a large electronegativity such fluoroanions and hexafluoro-anions. Fluoroanions may also be hygroscopic. If they possess strong hygroscopicity, then the potassium hydroxide is not required. Preferably, a DC current of about 3 volts and 60 milliamps per square inch of absorbent surface area is impressed across the electrodes. Preferably, the chamber contains a chimney and vent for venting evolved hydrogen outside of the chamber.

Optionally, the hearing aid battery can be charged as is further described in U.S. patent application Ser. No. 10/976, 490, now U.S. Pat. No. 7,705,558 and 60/516,205.

The invention of is used by: placing a hearing aid in need of dehumidification and sterilization in the chamber; allowing the electrochemical ozone generator to generate ozone from the moisture in and around the hearing aid, thereby dehumidifying the hearing aid; substantially confining the ozone in the chamber; and allowing the ozone to envelop and remain in contact with the hearing aid for a period of time sufficient to substantially disinfect said hearing aid. The invention may also generate ozone from ambient moisture inside the chamber that is adsorbed onto the separator of the ozone generator. The hearing aid battery may also be recharged.

Other objects, advantages, and novel features of the present invention will become more fully apparent from the following detailed description of the invention when considered in conjunction with the accompanying drawings, or may be learned by the practice of the invention as set forth herein.

BRIEF DESCRIPTION OF THE DRAWINGS

The present invention provides its benefits across a broad spectrum of applications. While the description, which follows hereinafter, is meant to be representative of a number of such applications, it is not exhaustive. As those skilled in the art will recognize, the basic apparatus taught herein can be readily adapted to many uses. This specification and the claims appended hereto should be accorded a breadth in keeping with the scope and spirit of the invention being disclosed despite what might appear to be limiting language imposed by the requirements of referring to the specific examples disclosed.

Referring particularly to the drawings for the purposes of illustrating the invention and its presently understood best mode only and not limitation.

DETAILED DESCRIPTION OF THE PREFERRED EMBODIMENTS

Referring now to the drawings wherein like reference numerals designate identical or corresponding parts throughout the several views, it is to be understood that the drawings are diagrammatic and schematic representations of various embodiments of the invention, and are not to be construed as limiting the invention in any way. The use of words and phrases herein with reference to specific embodiments is not intended to limit the meanings of such words and phrases to those specific embodiments. Words and phrases herein are intended to have their ordinary dictionary meanings, unless a specific definition is set forth at length herein.

Figures 1, 2:
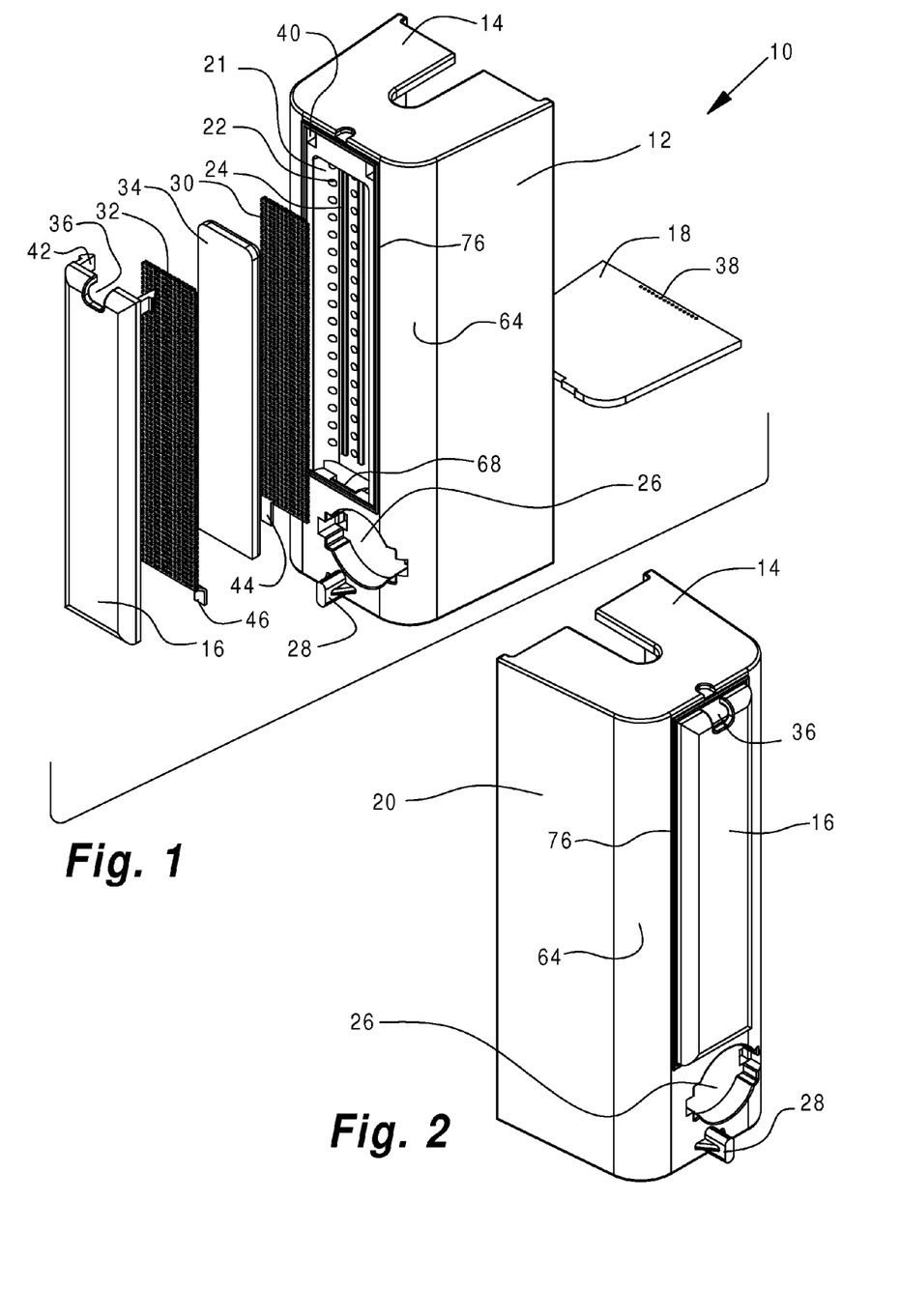
FIG. 1 is an exploded, top perspective view of a preferred embodiment of the invention.
FIG. 2 is an assembled top perspective view of a preferred embodiment of the invention.
Figures 3, 4:
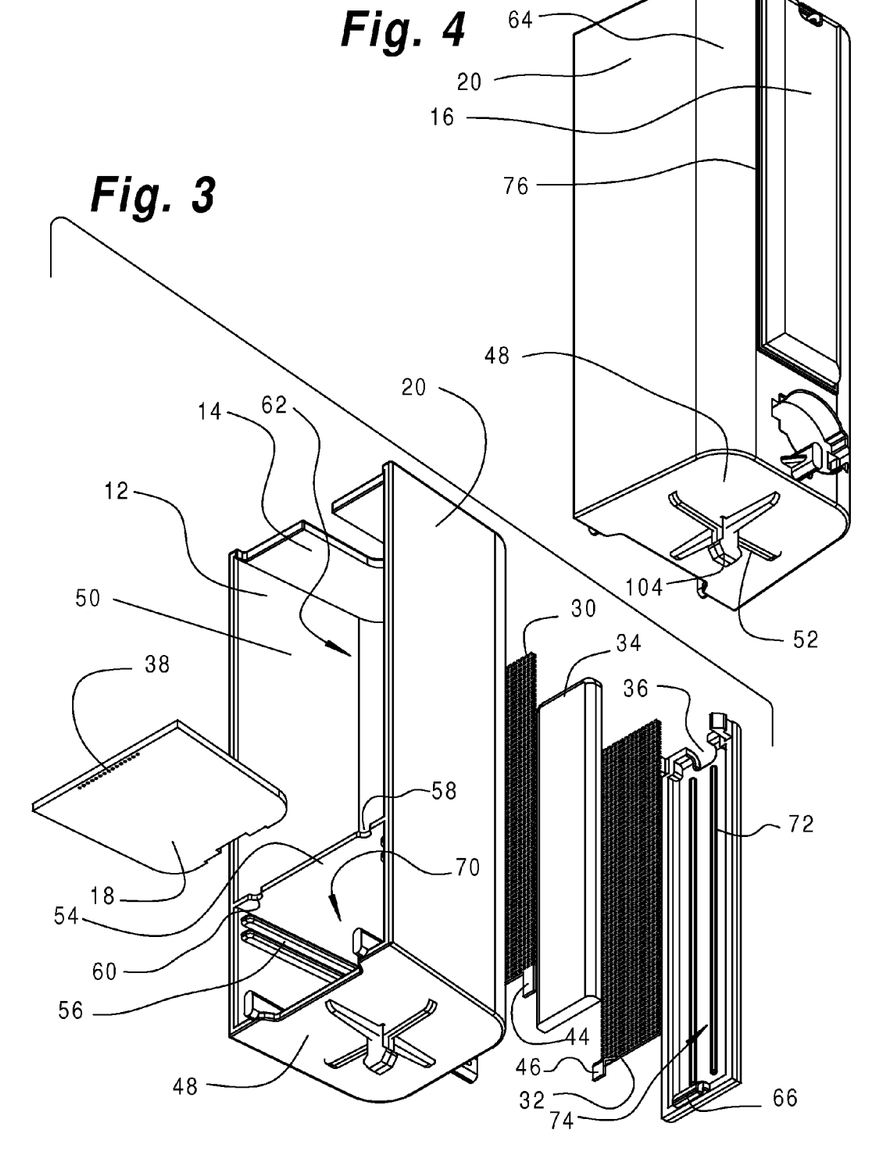
FIG. 3 is an exploded, bottom perspective view of a preferred embodiment of the invention.
FIG. 4 is an assembled bottom perspective view of a preferred embodiment of the invention.
Figure 5:
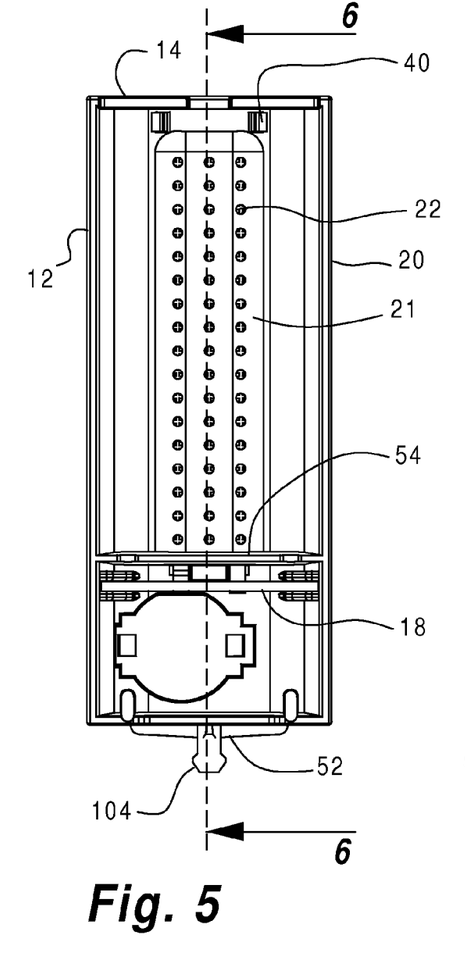
FIG. 5 is rear view of a preferred embodiment of the invention.
Figure 6:
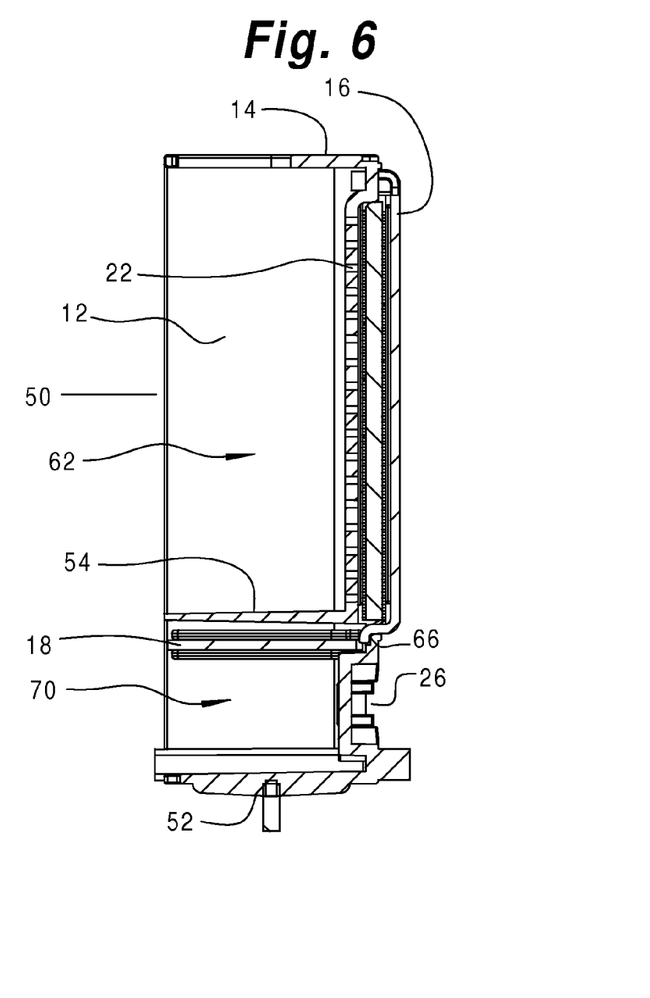
FIG. 6 is a cross section of a preferred embodiment of the invention along the lines 6-6 on FIG. 5.
Figure 7:
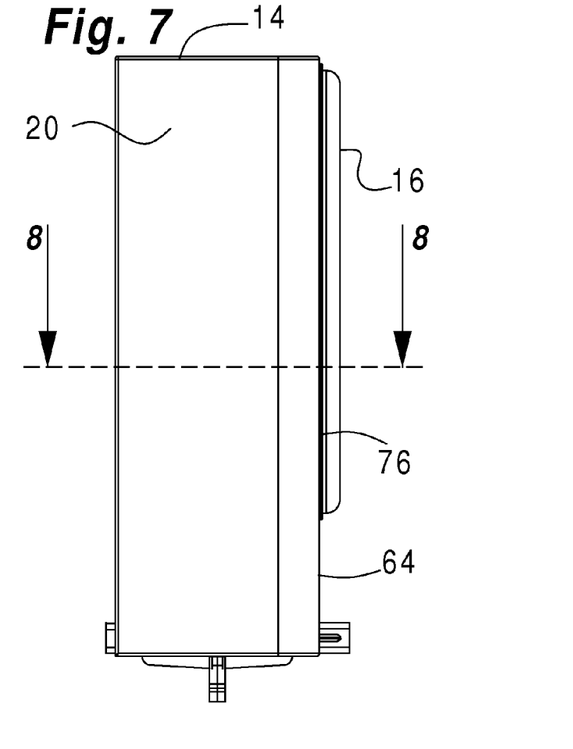
FIG. 7 is a side view of a preferred embodiment of the invention.
Figure 8:
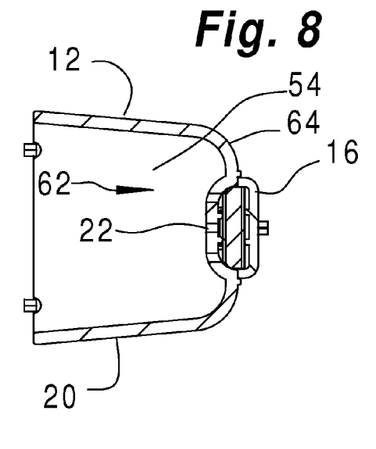
FIG. 8 is a cross section of a preferred embodiment of the invention along the lines 8-8 of FIG. 7.
Figure 9:
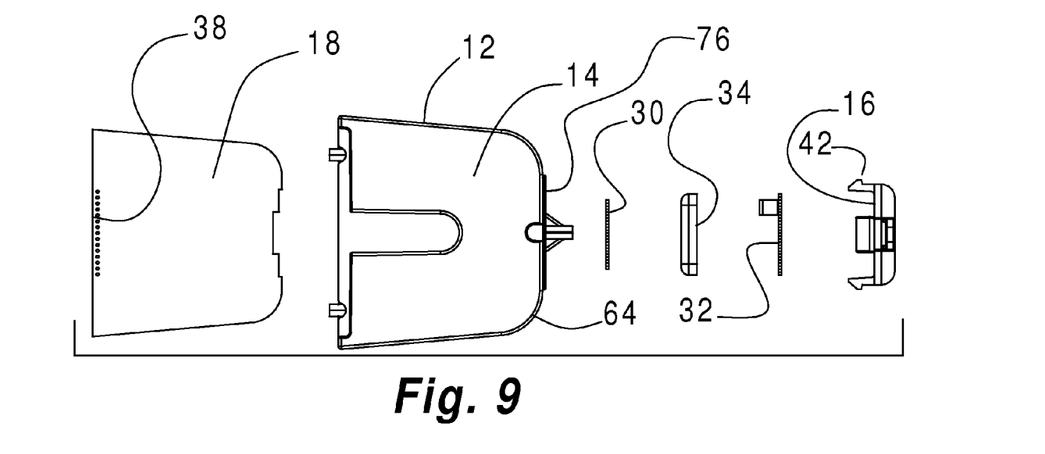
FIG. 9 is an exploded, top view of a preferred embodiment of the invention.
Figure 10:
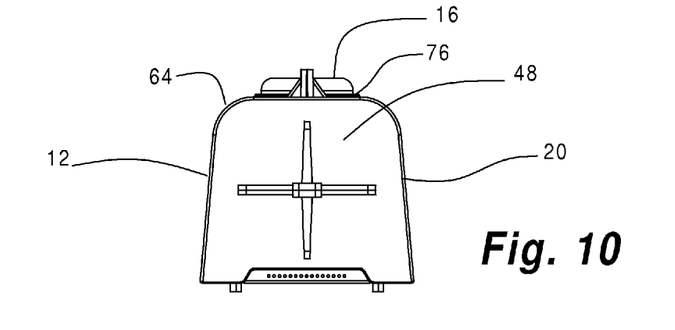
FIG. 10 is a bottom view of a preferred embodiment of the invention.
Figure 11:
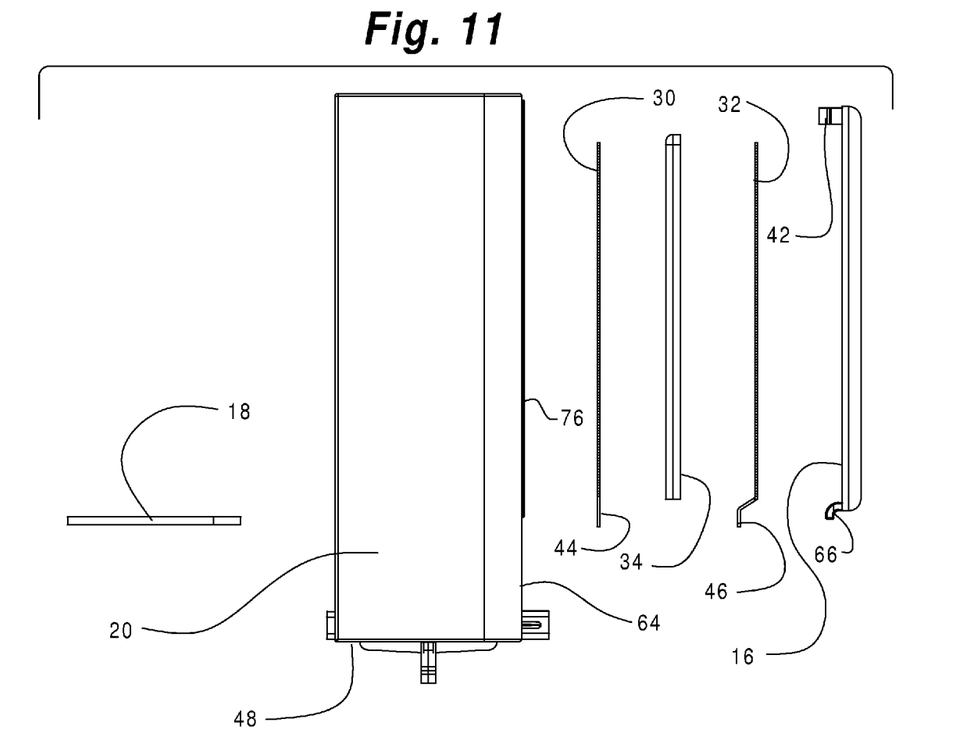
FIG. 11 is an exploded, side view of a preferred embodiment of the invention.
Figures 12, 13:
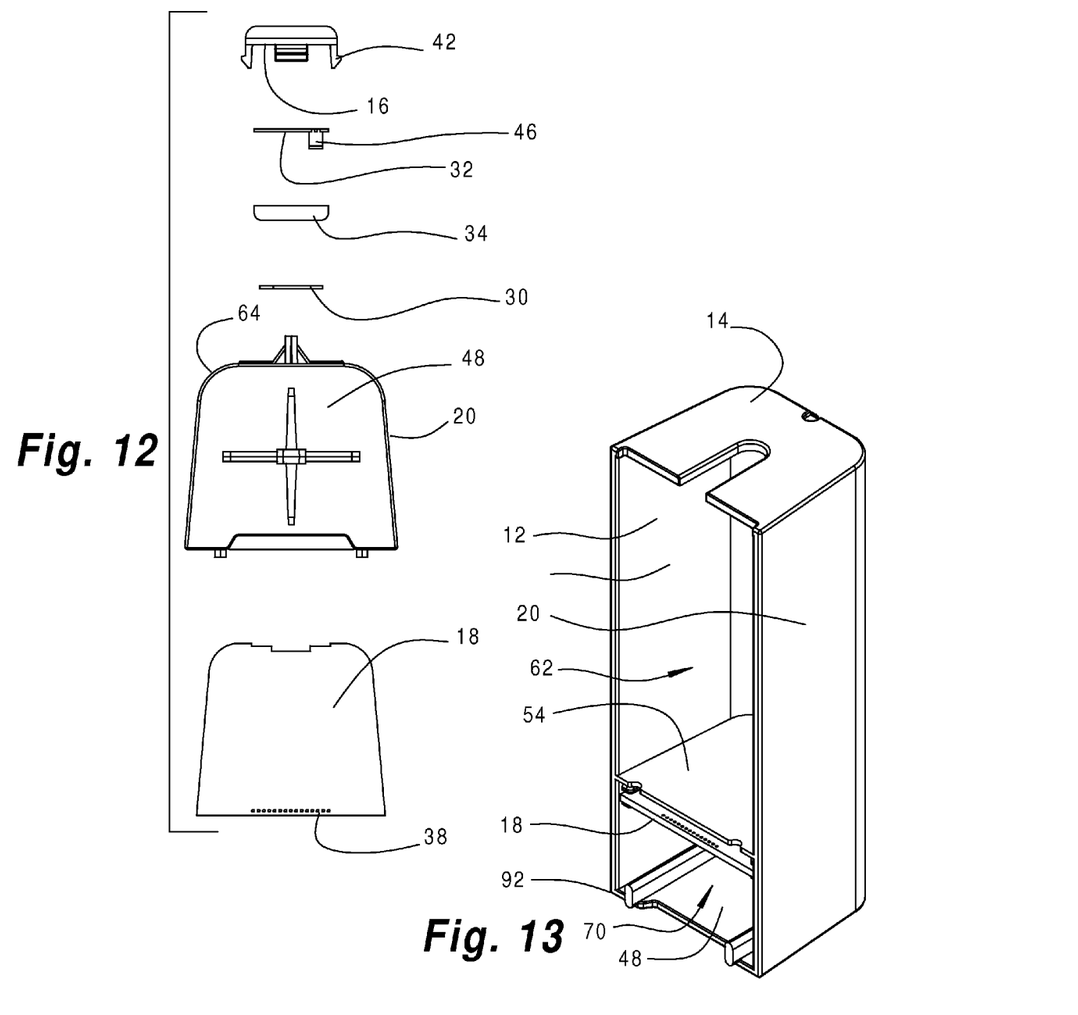
FIG. 12 is an exploded, bottom view of a preferred embodiment of the invention.
FIG. 13 is an assembled, rear perspective view of a preferred embodiment of the invention.
Figures 14, 15, 16:
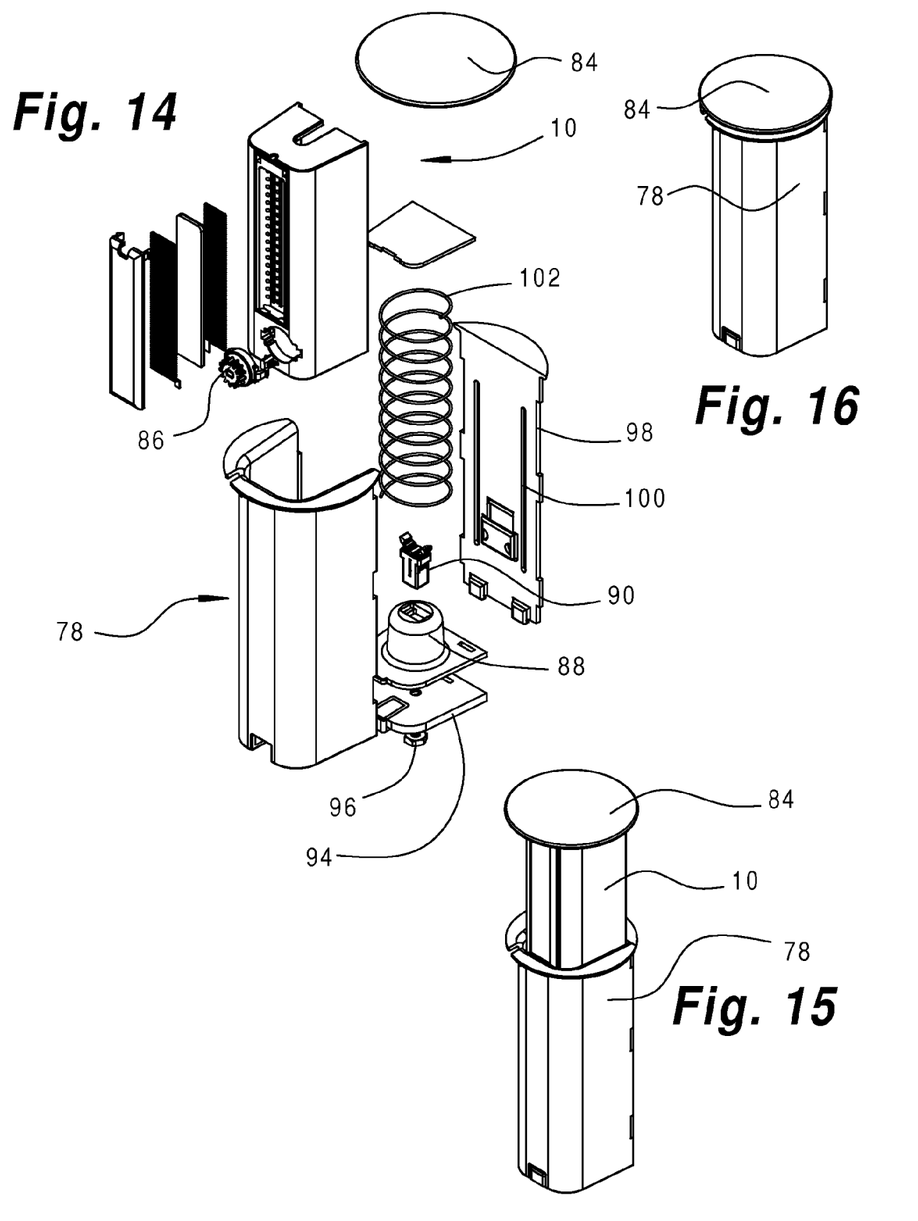
FIG. 14 is an exploded view of the chamber of this invention and its spring activated carrying tower.
FIG. 15 is an assembled view of the chamber of this invention in the open position within its carrying tower.
FIG. 16 is an assembled view of the chamber of this invention in the closed position within its carrying tower.
Figure 17:
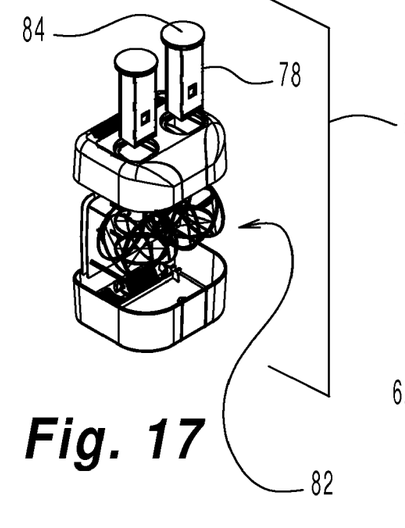
FIG. 17 is an exploded view of the housing for this invention.
Figure 18:
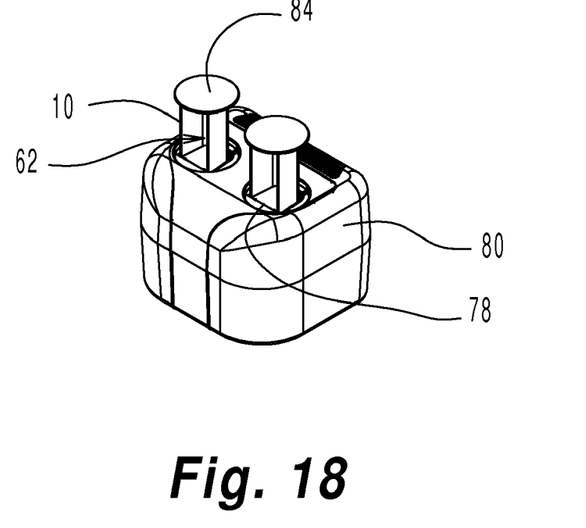
FIG. 18 is an assembled view of the completely assembled housing, chamber and carrying tower, with the carrying tower in the open position.
Figure 19:
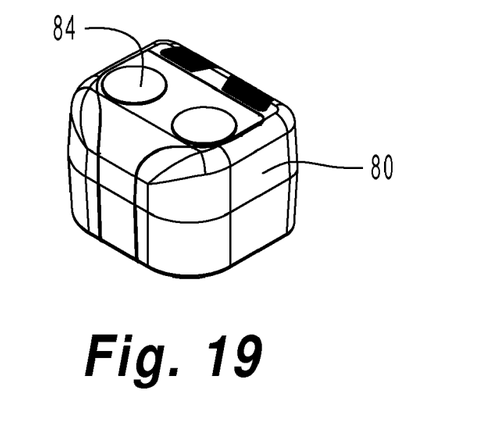
FIG. 19 is an assembled view of the completely assembled housing, chamber and carrying tower, with the carrying tower in the closed position.

There is illustrated generally at 10 a hearing aid dehumidifying and disinfecting chamber. The chamber 10 is designed as a drawer which slides inside a spring activated tower 78, which in turn is assembled inside a cabinet 80. The chamber 10 has a first side 12, a top 14, a second side 20, a front 21, a bottom 48 and an interior 62 which is designed to contain a hearing aid. One side 50 of the chamber 10 is open. This side 50 is closed by the rear 98 of the tower 78 when the chamber 10 is slid into it. When slid out of the cabinet 80 (see FIG. 18) the chamber 10 is in the open position. In this position the hearing aid can be inserted to or removed from the interior 62. When slid into the cabinet 80, the chamber 10 is in the closed position. In this position the hearing aid is dehumidified and sterilized as will be described. Optionally, the hearing aid battery can be charged as is further described in U.S. patent application Ser. Nos. 10/976,460 and 60/516,205. An array of antennae 82 are used to transmit energy to the hearing aid battery.

The tower 70 and chamber 10 are provided with grooves 100 and co-operating guides 28, 92 so as to provide smooth sliding over a defined path. This subassembly is provided with a spring 102, spring guides 52, 88 so as to bias the chamber 10 in an open position. A touch latch 90 and touch latch actuator 104 allow the chamber 10 to be opened and closed with a push on the top 14. A cap 84 attached to the top 14 provides a larger surface for pushing on.

The front 64 has a depression 21 that is perforated with a number of perforations 22. In front of the perforations 22 are an anode (the positive electrode) 30, a separator 34, a cathode (the negative electrode) 32 and a cover 16. The cover 16 fastens these components adjacent to each other and into the depression 21, aligned with the perforations 22 by means of a curved clip 66 and bayonet clips 42 on the rear of the cover 16 and co-operating recesses 40, 68 in the front 64. The anode 30, separator 34 and cathode 32 together form the ozone generator, as will become apparent.

Both electrodes 30, 32 are formed of wire mesh that is inert to the electrical and chemical environment of the chamber. Wire mesh is required so that water vapor and evolved gasses can pass through the electrodes 30, 32. Preferably the wire is nichrome, nichrome plated with platinum, stainless steel or stainless steel wire onto which lead dioxide is impressed. The cathode 30 has a tab 44 and the anode 32 has a tab 46. These tabs 44, 46 are used to connect the electrodes 30, 32 to a source of direct current or rectified alternating current. A DC current of about 2-3 V and 0.1 to 1.5 A/cm$^2$ is satisfactory. Any standard and well known method of providing electrical current can be employed in practice of this invention. The electronics are carried on a removable printed circuit board (PCB) 18 contained in an electronics compartment 70 within the chamber 10. Preferably the electronics will provide current regulation to the ozone generator so as to control its temperature. The electronics compartment 70 is separated from the interior 62 by a web 54. The PCB slides into the compartment 70 between rails 56, 60

The separator 34 is an absorbent electrically non-conductive, and chemically inert material. Adsorbed onto this is an electrolyte. The electrolyte is preferably comprised of a hygroscopic and ionic conductive material such as potassium hydroxide. In addition a non-hygroscopic and/or another hygroscopic electrolyte(s) possessing large electronegativity, such as fluoro-anions or hexafluoro-anions may also be adsorbed onto the separator 34. Alternatively, a polymer electrolyte membrane (PEM) can be used in place of the separator 34 with adsorbed electrolyte. This has several advantages. First, fluid management is simplified and the potential for leakage of corrosive liquids is eliminated. Second, the PEM/anode interface provides a chemical environment which is well-suited to the electrochemical $O_3$ reaction. Also, a PEM based on a fluoropolymer, such as a perfluorinated sulfonic acid, displays very high resistance to chemical attack.

When the separator 34 or PEM absorbs water vapor and thus is wetted with water, current will flow. The reaction that takes place at the anode 30 is as follows:

The reaction that takes place at the cathode is

The overall reaction in the generator is

The generator design and construction is such that at least 0.01 percent of the total evolved oxygen (x+y) is in the form of ozone.

Two ridges 24 in the depression 21 separate the anode 30 from the perforations 22 and facilitate migration of the ozone into the interior 62 of the chamber 10. Two ridges 72 inside the cover 16 form a path or chimney 74. A square seal 76 on the front seals the front 64 tightly against the cover 16 so that moisture from within the chamber 10 can communicate with the separator 34, hydrogen gas evolved at the cathode 32 can vent up the chimney 74 and ozone and oxygen gas evolved at the anode 30 can communicate with the inside 62 of the chamber 10.

Both dehumidification and sterilization are accomplished by the use this invention. Dehumidification is accomplished by electrochemical hydrolytic action upon the water vapor contained within the chamber 10. The water vapor is absorbed onto the separator 34 because of the attraction of the hygroscopic electrolyte. The adsorbed water is decomposed by current impressed across the electrodes to hydrogen gas, oxygen gas and ozone. The hydrogen gas vents up the chimney 74 to the outside. This creates a net movement of moisture laden air from inside the chamber 10 and from any hearing aid towards the ozone generator. In addition, the condensation of water vapor onto the hygroscopic matrix contained within the ozone generator also aids in a net movement of water vapor laden air toward the ozone generator. As the hygroscopic electrolyte is wetted by the moisture laden air, a current will begin to flow across the opposing electrodes 30, 32. This system is self-regulating in that current will only flow when there is moisture in the interior 62 of the chamber 10. When the chamber 10 contains no more moisture the hygroscopic electrolyte dries out and thus no more current flows.

Note that the ozone that is evolved from the anode 30 facilitates the dehumidification of the hearing aid by reducing surface tension of the moisture contained on and within the hearing aid. This greatly increases the surface area and therefore evaporative rate of the water.

Sterilization is accomplished by the evolution of a mixture of diatomic and triatomic oxygen (i.e. $O_2$ and $O_3$) from anode 30. As ozone is heavier than $O_2$ and air, it glides down the anode face and fills the interior 62 of the enclosure 10 which contains the hearing aid. Thus, the hearing aid is bathed in ozone laden air. As ozone is known to be one of the best sterilizing agents, the hearing aid is sterilized. As ozone is able to contact not only the outer encasement of the hearing aid, but it is able to enter the various internal compartments and cavities of the hearing aid, it will thus effect complete and total sterilization. This is important in that partial sterilization that results from UV exposure as described in the prior art not only is an ineffective and incomplete method of sterilization, but can facilitate the production of more virulent strains of the resident microorganisms as described above.

As high levels of ambient ozone can be a health hazard it should be noted that the instant invention is designed so as to impede the evolution of ozone from the device and into the ambient airspace. This is accomplished by providing a tightly sealed chimney 74 inside the cover 16 that vents hydrogen evolved from the cathode 32 through a vent 36. This design will pull in only a small amount of ambient air from the surrounding airspace and thus create a counter current airflow to restrict the evolution of ozone from the chimney 74. As ozone has a half-life of about 20 minutes, and the ozone generator will have decomposed essentially all of the water contained within the tower within about an hour, most if not all of the ozone will have been decomposed prior to the opening and retrieval of the hearing aid from its drying and recharging tower. Further, as the tower 78 is located within a larger enclosure 80, any ozone that escapes from the tower 78 will be sequestered within the larger enclosure 80. Further, the internal space of this larger enclosure 80 can be illuminated with short wavelength light (e.g., between 240 nm and 430 nm) generated by a light source such as an LED. As described above, this spectrum of light degrades ozone returning oxygen it to its diatomic ($O_2$) form. Such short-wavelength illumination thus further decreases the levels of ozone that may emanate from the device. Instructions provided with the invention will instruct users to leave their hearing aid within the closed chamber 10 for at least 6 hours. Alternatively, or in addition, an ozone sensor may be incorporated into the device. The sensor will inform the user when it is safe to retrieve the hearing aid from the tower 78 or allow a manual or automatic means to switch off the current provided to the ozone generator and thus eliminate ozone production prior to retrieval of the hearing aid.

The following reference numbers are referenced on FIGS. 1-19:
- 10 hearing aid disinfectant chamber—adapted to be used as a drawer in a cabinet with, optionally, an RF charging system
- 12 first side of chamber
- 14 top side of chamber
- 16 cover for ozone generator
- 18 printed circuit board
- 20 second side of chamber
- 21 depression for holding ozone generator
- 22 perforation
- 24 ridge inside depression
- 26 mounting hole for rotary damper
- 28 front vertical guide
- 30 anode
- 32 cathode
- 34 separator
- 36 hydrogen vent
- 38 connector for power and control signals
- 40 co-operating recess for bayonet clip
- 42 bayonet clip
- 44 electronic connection tab on anode
- 46 electronic connection tab on cathode
- 48 bottom of chamber
- 50 open side of chamber
- 52 upper spring guide
- 54 separator web
- 56 bottom rail
- 58 guide track relief
- 60 top rail
- 62 interior of chamber
- 64 front of chamber
- 66 curved clip
- 68 co-operating recess for curved clip
- 70 electronics compartment
- 72 ridge inside cover
- 74 chimney for hydrogen escape
- 76 seal for ozone generator
- 78 tower
- 80 cabinet
- 82 antennae
- 84 cap 86 rotary damper
88 touch latch mount and lower spring guide
90 touch latch
92 front vertical guide
94 nut guide
96 nut
98 rear of tower
100 groove
102 spring
104 touch latch actuator Thus it can be seen that with one simple device consisting of an ozone generator composed of an absorbent separator 34 sandwiched between two electrodes 30, 32 this invention solves two distinct problems: dehumidification and sterilization of hearing aids. Prior art may achieve a degree of dehumidification and sterilization but requires the use of at least two distinct and separate devices and mechanisms to function: i.e. desiccant that is consumed and must be frequently replaced and a UV lamp that only sterilizes exposed surfaces. The instant invention removes water vapor from the enclosure 10 by a consuming hydrolytic reaction, the resulting chemical product of which is ozone. The ozone is then used to sterilize the enclosed hearing aid. Further, when ozone is taken up by water vapor and droplets, water surface tension is drastically decreased. With surface tension diminished, the water droplets turn into thin sheets of water that have very high surface to volume ratio. The ozone induced sheeting therefore enables increased water vaporization thus facilitating the removal of water from the enclosed object. Further, as the water is now in the vapor phase, its migration toward the ozone generator is greatly facilitated by the steeply declining water vapor concentration gradient that is established by the strongly hygroscopic electrolyte (KOH) contained within the separator 34. Water vapor diffusion toward the ozone generator is also facilitated by the draft created by the rising of hydrogen, another reaction product of water vapor hydrolysis. The described means and art thus make a substantial improvement over prior art.

The present invention, by reason of co-generation of oxygen, substantially elevates the oxygen concentration within the chamber. It is known that a variety of microbes are killed by high concentrations of oxygen. This beneficial effect according to the present invention is in addition to the sterilizing action of ozone.

What has been described are preferred embodiments in which modifications and changes may be made without departing from the spirit and scope of the accompanying claims. Obviously, many modifications and variations of the present invention are possible in light of the above teachings. It is therefore to be understood that, within the scope of the appended claims, the invention may be practiced otherwise than as specifically described.

What is claimed is:

1. A hearing aid dehumidifier and disinfectant chamber comprising:
    an enclosure including a vapor permeable wall and being adapted to removably enclose a hearing aid;
    an electrochemical ozone generator in vapor transmitting relationship with said vapor permeable wall, said electrochemical ozone generator being adapted to draw water vapor from inside said enclosure and electrolyze it into at least ozone, said electrochemical ozone generator being positioned to discharge said ozone into said enclosure;
    the electrochemical ozone generator comprising:
    a wire mesh anodic electrode which is inert to the electrical and chemical environment of the electrochemical ozone generator; and
    a wire mesh cathodic electrode which is inert to the electrical and chemical environment of the electrochemical ozone generator; an absorbent, electrically non-conductive, and chemically inert separator, interposed between said anode and cathode; and a hygroscopic electrolyte adsorbed onto said adsorbent.

2. A hearing aid dehumidifier and disinfectant chamber as claimed in claim 1 in which the minimum percentage of ozone generated from said water vapor is 0.01.

3. A hearing aid dehumidifier and disinfectant chamber as claimed in claim 1 in which a DC current of about 2-3 V and 0.1-1.5 A/cm.sup.2 is impressed across said electrodes.

4. A hearing aid dehumidifier and disinfectant chamber as claimed in claim 1 in which said wire is selected from the group consisting of nichrome, nichrome plated with platinum, stainless steel and stainless steel onto which lead dioxide is impressed.

5. A hearing aid dehumidifier and disinfectant chamber as claimed in claim 1 in which said electrolyte comprises potassium hydroxide.

6. A hearing aid dehumidifier and disinfectant chamber as claimed in claim 1 further comprising a non-hygroscopic electrolyte possessing a large electronegativity adsorbed onto said adsorbent.

7. A hearing aid dehumidifier and disinfectant chamber as claimed in claim 6 in which said non-hygroscopic electrolyte is selected from the group consisting of fluoroanions and hexafluoro-anions.

8. A hearing aid dehumidifier and disinfectant chamber as claimed in claim 1 further comprising a vent adapted to output hydrogen, which is produced at said cathodic electrode, outside of said chamber.

9. A hearing aid dehumidifier and disinfectant chamber as claimed in claim 1 in which the battery in said hearing aid additionally has a radio frequency energy harvesting diode chargingly associated therewith; and
    said enclosure further has an open configuration and a closed configuration, said open configuration being adapted to the insertion and removal therefrom of said hearing aid, said closed configuration being adapted to providing radio frequency energy to said radio frequency energy harvesting diode as well as dehumidifying and disinfecting said hearing aid;
    further comprising a means for providing radio frequency energy to said radio frequency harvesting diode, when said enclosure is in said closed configuration, whereby said battery is charged.

10. A hearing aid dehumidifier and disinfectant chamber comprising:
    an enclosure means for removably enclosing a hearing aid;
    an electrochemical ozone generator means in vapor transmitting relationship with said enclosure, for drawing water vapor from inside said enclosure, electrolyzing it into at least ozone, and discharging said ozone into said enclosure;
    the electrochemical ozone generator means comprising:
    a wire mesh anodic electrode which is inert to the electrical and chemical environment of the electrochemical ozone generator;
    a wire mesh cathodic electrode which is inert to the electrical and chemical environment of the electrochemical ozone generator; an absorbent, electrically non-conductive, and chemically inert separator, interposed between said anode and cathode; and
    a hygroscopic electrolyte adsorbed onto said adsorbent.

11. A hearing aid dehumidifier and disinfectant chamber as claimed in claim 10 in which the minimum percentage of ozone generated from said water vapor is 0.01.

12. A hearing aid dehumidifier and disinfectant chamber as claimed in claim 10 in which a DC current of about 2-3 V and 0.1-1.5 A/cm.sup.2 is impressed across said electrodes.

13. A hearing aid dehumidifier and disinfectant chamber as claimed in claim 10 in which said wire is selected from the group consisting of nichrome, nichrome plated with platinum, stainless steel and stainless steel onto which lead dioxide is impressed.

14. A hearing aid dehumidifier and disinfectant chamber as claimed in claim 10 in which said electrolyte comprises potassium hydroxide.

15. A hearing aid dehumidifier and disinfectant chamber as claimed in claim 10 further comprising a non-hygroscopic electrolyte possessing a large electronegativity adsorbed onto said adsorbent.

16. A hearing aid dehumidifier and disinfectant chamber as claimed in claim 15 in which said non-hygroscopic electrolyte is selected from the group consisting of fluoroanions and hexafluoro-anions.

17. A hearing aid dehumidifier and disinfectant chamber as claimed in claim 10 further comprising a vent means for venting hydrogen, which is produced at said cathodic electrode, outside of said chamber.

18. A hearing aid dehumidifier and disinfectant chamber as claimed in claim 10 in which the battery in said hearing aid additionally has a radio frequency energy harvesting diode chargingly associated therewith; and said enclosure further has an open configuration and a closed configuration, said open configuration being adapted to the insertion and removal therefrom of said hearing aid, said closed configuration being adapted to providing radio frequency energy to said radio frequency energy harvesting diode as well as dehumidifying and disinfecting said hearing aid;

further comprising a means for providing radio frequency energy to said radio frequency harvesting diode, when said enclosure is in said closed configuration, whereby said battery is charged.

* * * * *